United States Patent [19]

Dragone

[11] Patent Number: 4,670,010
[45] Date of Patent: Jun. 2, 1987

[54] LIQUID-NEBULIZING DEVICE FOR THE DERMATOLOGICAL TREATMENT OF THE HANDS

[76] Inventor: Giorgio Dragone, Via Redaelli, 2, 22057 Olginate (Como), Italy

[21] Appl. No.: 710,152

[22] Filed: Mar. 7, 1985

[30] Foreign Application Priority Data

Mar. 26, 1984 [IT] Italy .............................. 21362/84[U]

[51] Int. Cl.⁴ ............................................ A61M 35/00
[52] U.S. Cl. ...................................... 604/289; 4/623; 128/368; 239/127; 422/28; 422/292
[58] Field of Search ................ 604/289, 290, 23, 24; 128/365–368, 371, 375; 4/DIG. 3, 623–626, 304, 305; 422/28, 106, 292; 239/124, 127, 332; 119/159, 160

[56] References Cited

U.S. PATENT DOCUMENTS

| | | |
|---|---|---|
| 2,608,952 | 9/1952 | Herbert .............................. 119/159 |
| 2,814,081 | 11/1957 | Stevenson .......................... 422/292 |
| 2,938,495 | 5/1960 | Hinton ................................ 604/289 |
| 3,147,767 | 9/1964 | Goss .................................... 239/127 |
| 3,565,065 | 2/1971 | Biggs . | 
| 3,599,251 | 8/1971 | Wright . |
| 3,780,942 | 12/1973 | Scharfenberger ................... 239/127 |
| 4,061,271 | 12/1977 | Kimbrough ......................... 239/127 |
| 4,119,439 | 10/1978 | Boucher ............................. 128/366 |
| 4,144,596 | 3/1979 | Macfarlane . |
| 4,300,556 | 11/1981 | Ochi et al. .......................... 128/368 |
| 4,331,137 | 5/1982 | Sarui . |
| 4,402,095 | 9/1983 | Pepper ................................... 4/623 |

FOREIGN PATENT DOCUMENTS 3025273 1/1981 Fed. Rep. of Germany ...... 422/292
8300645 3/1983 PCT Int'l Appl. .................. 422/28

*Primary Examiner*—C. Fred Rosenbaum
*Assistant Examiner*—Mario Costantino
*Attorney, Agent, or Firm*—Browdy and Neimark

[57] ABSTRACT

The invention concerns the technical field of apparata for dispensing liquids over different parts of the human body, either for disinfection or therapeutic purposes, and relates to a liquid-nebulizing device for the dermatological treatment of the hands.

The technical problem to be solved was that of providing a device which could nebulize liquids and readily irrigate in a fully automated manner the entire surface of a skin portion exposed, in particular the hand palms.

The solution to the problem is provided by a device having a housing (2) which comprises a cavity (4a) bound by at least one top roof or cover (6), whereat an infrared light sensor (34) is arranged which responds to the presence of hands located in its direct proximity, and a bottom plate (8) engaging a spray nozzle or atomizer (18) operative to nebulize the liquid to be dispensed in a direction toward said roof (6).

9 Claims, 7 Drawing Figures

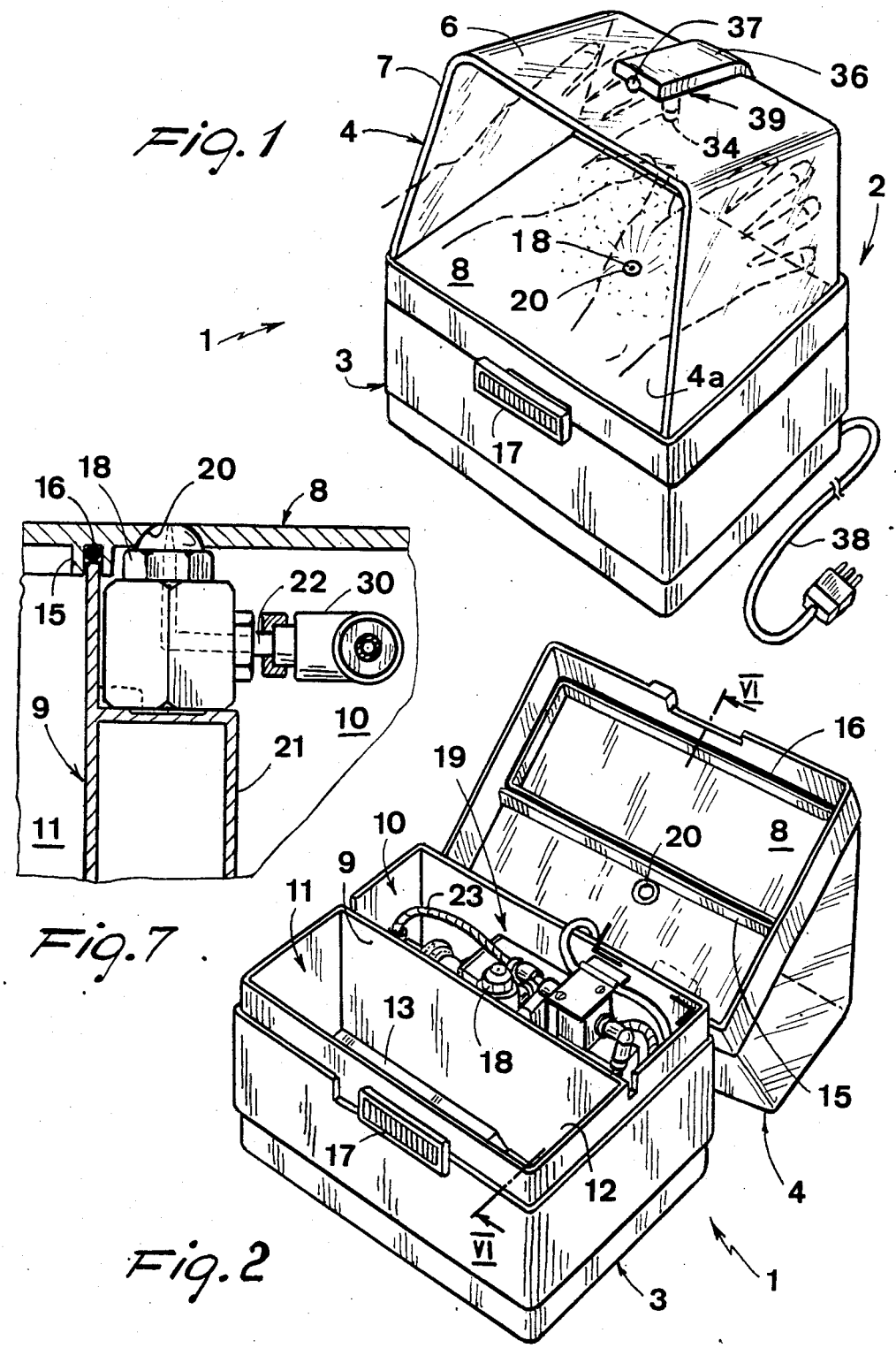

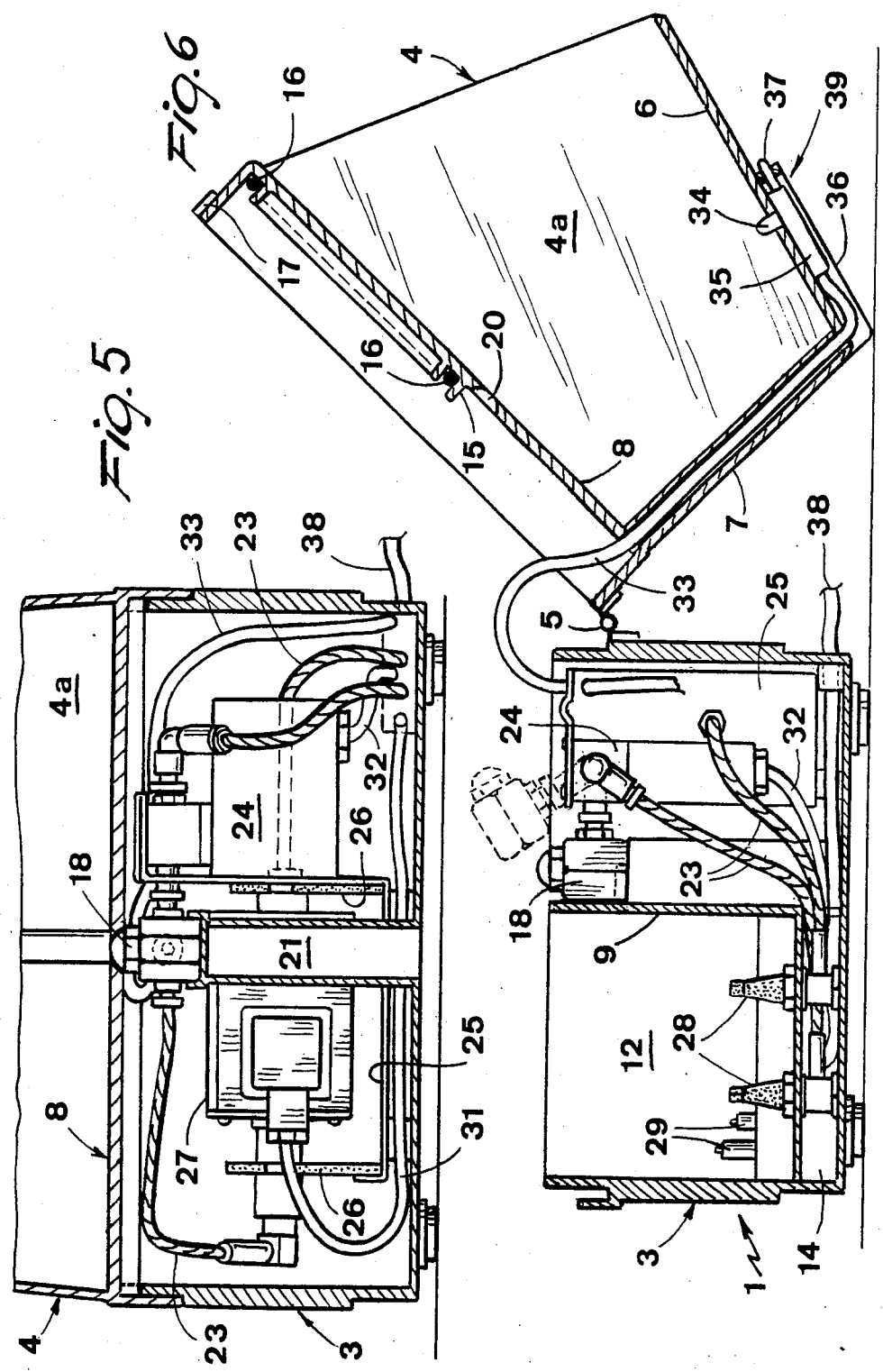

LIQUID-NEBULIZING DEVICE FOR THE DERMATOLOGICAL TREATMENT OF THE HANDS

BACKGROUND OF THE INVENTION

The invention relates to a liquid-nebulizing device for the dermatological treatment of the hands, e.g. by dispensing detergent and/or disinfectant and/or therapeutic liquids.

As is known, some apparata have been developed which can sprinkle or nebulize liquids of various description over different parts of the human body, such as the face or limbs. In this connection, reference can be made to U.S. Pats. Nos. 3,565,065; 3,599,251; 4,144,596; and 4,331,137. These prior patents disclose apparata which can dispense a variety of liquids for medical or disinfection uses by anyone involved on account of his/her activity in contacts with a large number of people or special environments, and is to avoid contagion or becoming a contagion carrier.

Such prior apparata are only moderately successful when used for the dermatological treatment of the hands, even where expressly designed for this specific application; disadvantages are experienced with such apparata which affect adversely their usefulness.

It should be pointed out, in fact, that the effectiveness of a treatment can only be judged satisfactory where the liquids are nebulized and not merely sprinkled over, and where the same are dispensed to impinge on and sweep across most of the hand skin surface, in particular the hand palms.

This is so because only nebulization can ensure deep penetration of the liquid droplets into the skin and optimum hygienic conditions because no liquid build-ups are produced and no devices are required for collecting and discharging the spent liquids. Nebulization also makes unnecessary hand drier devices, which devices are exposed to contamination and, in any case, would shorten the time of residence of the liquids on the skin. Irrigation should affect most of the hand skin surface because otherwise, even a massage directed to spread the liquid evenly is inadequate to ensure proper spreading.

Lastly, it is the hand palms that mostly require irrigation because they are more likely to come into direct contact with external objects.

With prior apparata, the above-outlined problems are caused by the very fact that the liquids are often just sprinkled over and not nebulized, by that even where nebulization of the liquids is provided the same would only sweep randomly the exposed skin surface, and by that the irrigation is more likely to concern the back of the hands than the palms. This because the delivery cone of any sprinkler or nebulizer has a breadth which varies considerably from the starting point of delivery, and because a user is allowed to place his/her hands at any regions of the delivery cone, even where the latter is quite small. The net result is that the irrigation effect can only occasionally concern the entire skin surface of the hands, while owing to the user tending to bring his/her hands closer to the spray nozzles, an even more limited portion of the skin surface is actually irrigated. Furthermore, the spray and nebulizing nozzles are generally arranged and oriented without taking into due account the fact that hands are spontaneously introduced into the treatment area in a palm-down attitude. And in general, the spray and nebulizing nozzles are arranged to act from above, with the consequence that it is mainly the back of the hand which is irrigated, i.e. a portion of the skin surface of no primary concern from the standpoint of the required treatment.

It should be further noted that an added disadvantage of prior apparata comes from that they have in general a significant operating inertia, which requires an ample time interval between successive cycles. In fact, on interrupting their operation, as at the end of an operating cycle, one is to wait for the already started but not yet dispensed mass of liquid to flow down. After this time has elapsed, one can again operate a known apparatus, but more time must be conceded for the liquid to be pressurized and delivered. This shortcoming imposes limitations on the practical use of known apparata in medical ambulatories and wherever continued utilization of the apparata by a number of persons is imperative.

Prior apparata, moreover, are relatively complex, expensive and bulky, and accordingly, basically unsuited to the widespread application thereof which would be highly desirable for hygienic reasons.

SUMMARY OF THE INVENTION

In view of the above situation, it is a primary object of this invention to provide a device for the dermatological treatment of the hands which can substantially obviate the cited prior shortcomings.

This object is achieved by a liquid-nebulizing device for the dermatological treatment of the hands, comprising a rigid outer housing having a cavity for introduction of the hands, therein, a reservoir containing a suitable liquid for said treatment, a spray nozzle operative to dispense said liquid, a pumping unit operative to pick up said liquid from said reservoir and pump it to said spray nozzle, and members driving said pumping unit, the device being characterized in that said housing is configured in part as a dome defining on its interior said cavity, that said dome comprises at least one top roof whereat said driving members are located, and a bottom plate whereat said spray nozzle is located, and in that said spray nozzle is effective to nebulize said liquid and positioned to direct said liquid toward said top roof.

BRIEF DESCRIPTION OF THE DRAWINGS

Further features and advantages will be more clearly understood from the following description of a preferred embodiment of the invention, with reference to the accompanying drawings, where:

FIG. 1 shows a perspective view of the device according to the invention, in a position for use thereof, with the hands of a user being shown in phantom lines;

FIG. 2 shows the same device as FIG. 1, in an open position thereof with a domed portion tilted out from a base portion of the device;

FIG. 5 is a further sectional view of this device, taken along the line V—V of FIG. 3;

FIG. 6 shows this device in the open position of FIG. 2 and as sectioned along the line VI—VI of FIG. 2; and FIG. 7 is a detail view of this device, to an enlarged scale from the preceding figures.

DESCRIPTION OF THE PREFERRED EMBODIMENT

Figure 3:
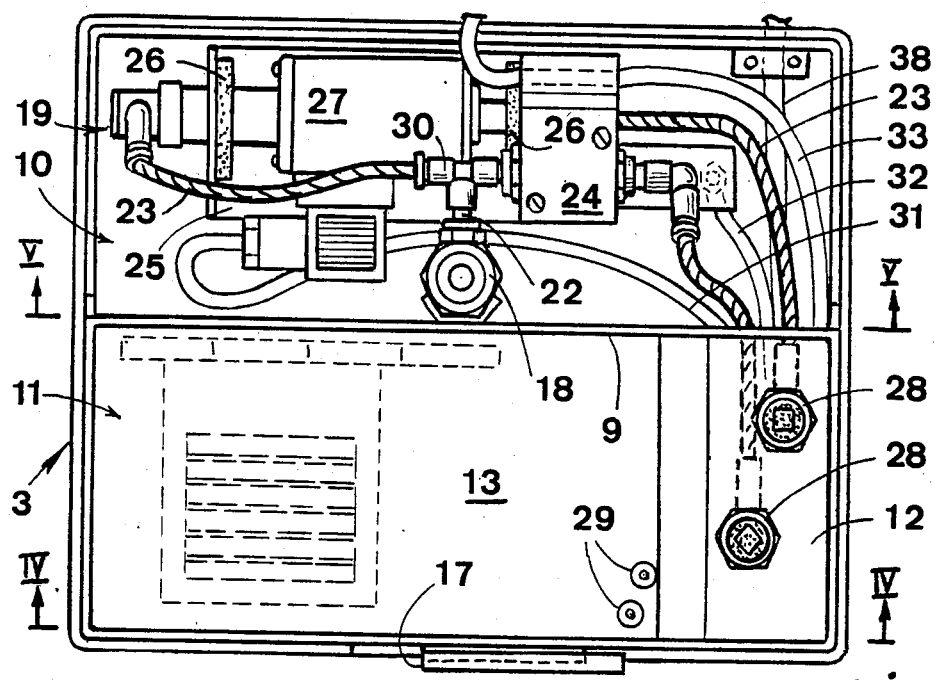
FIG. 3 is a top plan view of the base of FIG. 2.

With reference to the drawing figures, a device according to this invention is generally designated therein with the reference numeral 1. It comprises a housing 2 consisting of a portion surrounded by base 3 and a portion surrounded by dome or hood 4 enclosing a cavity 4a and being connected to the base 3 by hinges 5, best shown in FIG. 6. The hinges 5 are arranged to permit of the dome or hood 4 being tilted out or opened from the base 3. This tilting movement leaves the base 3 exposed because the hood 4 is defined by a top cover or roof 6, three sidewalls 7, and bottom plate 8 which closes the base 3.

The base 3 is divided substantially in two adjacent compartments by a partition 9 which defines a first zone 10 for various elements determining the machine operation, and a second zone 11 which comprises a tray 12 forming the reservoir for the liquid to be dispensed. Below the tray 12 and bottom 13, there is provided a space 14 for accommodating electrical devices cooperating with the various elements located in the first zone 10.

The hood 4 and base 3 may be engaged with each other in a substantially tight, sealed relationship. More specifically, it is contemplated that the bottom plate 8 of the hood 4 have its bottom face shaped to match the top edges of and to cover the base 3. As shown in FIG. 6, the bottom plate 8 has ribs 15 and a seal 16 confronting the base 3 and effective to make a seal with the tray 12. The hood 4 and base 3 can be made to close fast with each other by means of a releasable interlock defined by a slider 17 mounted slidably to connect small blocks together which project from the hood 4 and base 3, respectively. The first zone 10 accommodates a spray nozzle 18 and a pumping unit 19 operative to pick up the liquid from the tray 12 and deliver it to the spray nozzle 18.

The spray nozzle 18 is essentially a nozzle of the same general type as used with oil burners and capable of finely atomizing the liquid being delivered to it, in a manner known per se. The construction of the spray nozzle 18 is shown best in FIG. 7, the nozzle being aimed upwards, i.e. at the roof 6 of the hood 4.

The spray nozzle 18 is in contact with the bottom plate 8, it engaging with a hole 20 formed centrally thereto and shaped to mate with the top end of the spray nozzle. Furthermore, the spray nozzle 18 is supported on a columnar extension 21 of the partition 9 by merely resting on it.

Shown in phantom lines in FIG. 6 is how the spray nozzle 18 can be raised from the columnar extension 21 with the bottom plate in its tilted out position. In operation, a steady mounting of the spray nozzle 18 is provided by the same bearing against the bottom plate 8 at one end and the columnar extension 21 at the other end.

Liquid to be nebulized is supplied to the spray nozzle 18 through a branch line or conduit 22 extending from the junction between conduits 23a and 23b. Together, conduits 23a, 23b and 23c form a circuit of substantially looped configuration and serially interconnecting the tray 12 with the pumping unit 19. The latter (FIG. 3) includes a pulse or vibration pump 27 and a solenoid valve 24. The pulse pump 27 operates on AC current has a separate inlet and outlet port (40, 41, respectively) and is known per se. The solenoid valve 24 is inserted in the conduit 23b between the tray 12 and pulse pump 27, on the delivery side of the latter. Also, the solenoid valve 24 is directly consecutive to the branch line or conduit 22, which is inserted between the solenoid valve and outlet port of pulse or vibration pump 27.

The solenoid valve 24 is structured such that when in the open position, the liquid flowing through the conduits 23a, 23b and 23c can freely flow back into the tray whence it had been drawn. With the solenoid valve in the closed position, the only available course left to the liquid drawn from the tray 12 and flowing through the conduits 23c, then 23b is the branch line 22 leading to the spray nozzle 18.

Figure 4:
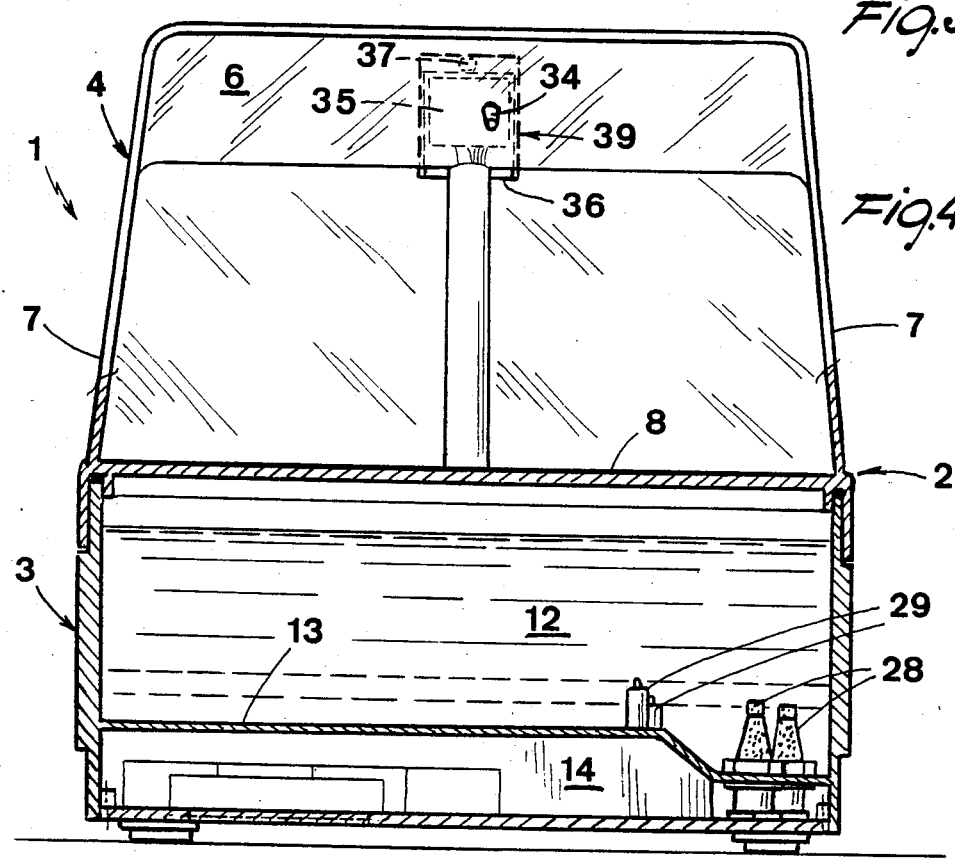
FIG. 4 is a sectional view of the device in the closed position of FIG. 1, as taken along the line IV—IV of FIG. 3.

As shown in FIGS. 3 and 4, in particular, the solenoid valve 24 is supported on a small rigid frame 25 attached to the base 3, and the vibration pump 27 is connected to the frame 25 through flexible mounts 26 adapted to dampen the pump vibrations.

The conduits 23b and 23c open with two directly contiguous ends into the tray 12, at filters 28, made preferably of a sintered metal material. The filters are located at a recessed area of the tray 12, as shown in FIGS. 3, 4 and 6. These figures also show how the tray 12 is provided with fixed level sensors 29 adapted to establish a mutual electric contact according to the level of the liquid in the tray 12. FIGS. 3 and 7 show a connection element 30 interconnecting the conduits 23a and 23b and branch line 22. The conduits 23a, 23b and 23c are engaged with the connection element 30, filters 28, vibration pump 27, and solenoid valve 24 by simple quick-release push-in fittings.

Located at the top of the cavity 4a, defined by the hood 4, activating members 39 connected to the electric apparata housed in the space 14. These apparata establish, in a manner known per se, an electric connection between an electric supply cable 38, level sensors 29, activating members, and pumping unit 19. FIGS. 3, 5, 6 show that from the space 14 there extend a supply cable 38, a first cable 31 for connection to the vibration pump 27, a second cable 32 for connection to the solenoid valve 24, and a third cable 33 for connection to the activating members 39 which reaches the roof 6 of the hood 4.

The activating members 39 include, as a basic component thereof, and a proximity sensor, realized by infrared light sensor 34 which protrudes from a small board 35 having a printed circuit thereon, known per se and serving the sensor 34 itself. The sensor 34 would be calibrated to control starting of the vibration pump 27 and closing of the solenoid valve 24 only on sensing the presence of hands or objects placed in its direct proximity. Should the hands be placed adjacent the bottom plate 8, the infrared light sensor 34 would remain inoperative.

Constructionally, the sensor 34 is passed through the roof 6 and the board 35 is located on the exterior of the roof, being shielded by a covering element 36 of box-like configuration whence an indicator 37 stands out which is joined to the board 35. The indicator 37 is controlled by the level sensors 29 and arranged to change its color in accordance with a signal supplied by the level sensors 29.

The device of this invention operates as follows. In the rest condition, the vibration pump 27 would be inoperative and the solenoid valve 24 open, thus enabling free flowing of the liquid through the circuit defined by conduits 23a, 23b and 23c. If the tray 12 is substantially filled up, as shown in FIG. 4, then both level sensors 29 are covered by the liquid and in electric contact with each other, and the indicator 37 has one color, e.g. green. If on the contrary, the liquid level in the tray 12 drops until the electric contact between the level sensors 29 is broken, the indicator 37 will show a different color, e.g. red, to warn that the tray 12 is to be topped up. This would be done immediately and simply by first sliding the slider 17 aside and tilting the hood 4 open from the base 3: thus, the tray 12 is exposed and can be filled with a suitable liquid, such as a bactericide liquid for operating rooms.

On introducing the hands into the cavity 4a, close to the roof 6, the infrared light sensor 34 will detect this and start the whole device. By contrast, should the hands be mistakingly placed next to the bottom plate 8, i.e. adjacent the spray nozzle 18, the infrared light sensor 34 would not be energized. The cited activating members, of which the sensor 34 is a part, control the vibration pump 27 to start and the solenoid valve 24 to close. In this condition, the liquid flowing through the circuit defined by conduits 23a and 23b of looped configuration is forced out of the spray nozzle 18.

The nulizing action is carried on as long as the sensor 34 is energized; on withdrawing the hands from the cavity, the solenoid valve 24 is immediately opened and the vibration pump 27 stopped.

Opening of the solenoid valve 24 brings about immediate discontinuance of the delivery of liquid from the spray nozzle 18, since the liquid, still in a pressurized condition, is allowed to drain off into the tray 12 without any serious loss of load, because no elements like the spray nozzle 18 are provided along conduit 23b. All of the liquid still present in the conduit 23b downstream of the vibration pump 27 will then tend to flow to the tray 12 and nebulization is discontinued immediately.

Also immediately can the liquid be put again under pressure on closing the solenoid valve 24 and operating the vibration pump 27; the amount of the liquid that should be pressurized is minimal and corresponds to that included between the pump 27 and solenoid valve 24 in conduit 23a.

The invention affords many important advantages.

The delivered product, in a finely nebulized form, is always spread over a broad area of the hand skin surfaces owing to the setting of their distance from the spray nozzle 18. Further, the location of the spray nozzle 18 at the base of the hood 4 allows for a spontaneous introduction of the hands palms down; thus, it is the hand palms that are first irrigated.

It should be also noted that any cleaning operations may be carried out on the bottom plate 8 while the device is in a potentially operative condition, because the sensor 34 would not be energized by the presence of hands at the level of the bottom plate 8.

The device of this invention has shown to be very quick to operate, and accordingly, may be used even where a large number of potential users is anticipated per unit, such as in hospitals, communities, etc.

The device as a whole is of simple construction and easy to keep clean; as an example, direct access to the tray 12 is gained by tilting open the hood 4, and all the internal parts can be readily removed and reassembled by virtue of the cited fast connection of the push-in type. The spray nozzle 18 could also be lifted off its support without actually removing it. On the whole, this device gives full assurance of being hygenic.

I claim:

1. A liquid-nebulizing device for the dermatological treatment of hands, comprising:

a rigid housing, said rigid housing including a first portion defining a cavity for the introduction of hands therein;

a second portion, said second portion including a reservoir for a dermatologically acceptable liquid, a spray nozzle adjacent to or extending into said cavity for nebulizing said liquid into said cavity, a pump having separate inlet and outlet ports, a first conduit extending between said inlet port and said reservoir, a second conduit extending between said outlet port and a junction, a third conduit, extending from said junction to said spray nozzle, a fourth conduit extending between said junction and said reservoir, and a solenoid valve positioned along said fourth conduit;

and activating means within said cavity for said pump, comprising a proximity sensor in electrical communication with said pump and said solenoid valve, for detecting the presence of a hand at a predetermined position within said cavity, said activating means, including means for causing said pump to operate while closing said solenoid valve when a hand is present within said cavity, and means for causing said pump to cease operation while opening said solenoid valve when a hand is removed from within said cavity.

2. The device of claim 1 wherein said first portion is dome-shaped and positioned above said second portion, said proximity sensor overhangs said cavity and is calibrated to activate said pump when said hand is placed closer to said proximity sensor than to said nozzle.

3. The device of claim 2 wherein said first and said second portions are separated by a bottom plate and said spray nozzle is positioned in correspondence with said bottom plate and is directable toward said proximity sensor.

4. The device of claim 2 wherein said pump is a pulse pump.

5. The device of claim 2 wherein the bottom of said dome-shaped first portion is fixed to and covered by said bottom plate;

said second portion is mounted within a base; and said dome-shaped first portion, with said bottom plate fixed thereto, is connected by a hinge means to an edge of said base and is tiltable upon said hinge means from a closed position, where said bottom plate rests upon and covers said base, to an open position, where said bottom plate contacts to said base essentially only at said edge of said base;

said bottom plate defining a central hole corresponding to said spray nozzle when said dome-shaped first portion is in a closed position.

6. The device of claim 5 wherein said second portion further comprises a partition, transverse to said bottom plate, defining a first zone comprising said reservoir and second zone comprising pump, said third conduit and said spray nozzle, said first and fourth conduits extending across said first and second zones.

7. The device of claim 6 wherein said spray nozzle extends upwardly, is supported on a columnar extension of said partition, and ends in close proximity to said hole when said dome-shaped first portion is in a closed position.

8. The device of claim 7 wherein said bottom plate includes, on a side opposing said cavity, a rib provided with a seal for engaging with and sealing said reservoir when said dome-shaped first portion is in a closed position.

9. The device of claim 8, wherein a space is defined between said base and the bottom of said reservoir, and said first and fourth conduits extend through said space.

* * * * *